United States Patent
Reich et al.

(10) Patent No.: US 7,132,275 B2
(45) Date of Patent: Nov. 7, 2006

(54) MULTIFUNCTIONAL MAGNETIC NANOWIRES

(75) Inventors: Daniel Reich, Baltimore, MD (US); Gerald Meyer, Baltimore, MD (US); Chia-Ling Chien, Lutherville, MD (US); Christopher Chen, Baltimore, MD (US); Peter C. Searson, Balto, MD (US)

(73) Assignee: The John Hopkins University, Baltimore, MD (US)

( * ) Notice: Subject to any disclaimer, the term of this patent is extended or adjusted under 35 U.S.C. 154(b) by 210 days.

(21) Appl. No.: 10/143,813

(22) Filed: May 14, 2002

(65) Prior Publication Data

US 2002/0187504 A1 Dec. 12, 2002

Related U.S. Application Data

(60) Provisional application No. 60/336,718, filed on Dec. 7, 2001, provisional application No. 60/290,338, filed on May 14, 2001.

(51) Int. Cl.
  C07H 21/04 (2006.01)
  C12Q 1/68 (2006.01)
(52) U.S. Cl. .............. 435/287.1; 536/23.1; 536/24.3; 977/704; 977/728; 977/769
(58) Field of Classification Search .............. 435/6, 435/91.1, 91.2, 287.2; 428/323; 437/233
  See application file for complete search history.

(56) References Cited

U.S. PATENT DOCUMENTS 5,200,084 A * 4/1993 Liberti et al. .............. 210/695
5,897,945 A * 4/1999 Lieber et al. .............. 428/323
6,066,448 A * 5/2000 Wohlstadter et al. .......... 435/6
6,506,564 B1 * 1/2003 Mirkin et al. .................. 435/6
2004/0209376 A1 * 10/2004 Natan et al. ................. 436/56

FOREIGN PATENT DOCUMENTS

WO   WO 98/05920    * 2/1998
WO   WO01/23645 A1 * 4/2001

OTHER PUBLICATIONS

Sellmyer et al. J. Phys. Condens, Matter, vol. 13, pp. R433-R460, Jun. 2001.*
Richter et al. Applied Physics Letters, vol. 78, No. 4, pp. 536-538, Jan. 2001.*
Kirsch et al. Thin Solid Films, vol. 305, pp. 248-253, 1997.*
Pompe et al. Z. Metalikd. vol. 90, pp. 1085-1091, 1999.*
Mbindyo et al. Adv. Mater. vol. 13, No. 4, pp. 249-254, Feb. 2001.*
Keating et al. (Abstracts of Papers, American Chemical Society, 220th, IEC-117, Aug. 20-24, 2000).*
Martin et al. (Abstracts of Papers, American Chemical Society, 220th, IEC-145, Aug. 20-24, 2000).*
Mbindyo et al. (Abstracts of Papers, American Chemical Society, 220th, IEC-145, Aug. 20-24, 2000).*

* cited by examiner

*Primary Examiner*—Jeanine A. Goldberg
(74) *Attorney, Agent, or Firm*—Whitham, Curtis, Christofferson & Cook, P

(57) ABSTRACT

The invention provides multisegmented, multifunctional magnetic nanowires for the probing and manipulation of molecules at the cellular and subcellular level. The different segments of the nanowire may have differing properties, including a variety of magnetic, non-magnetic, and luminescent behavior. Differences in surface chemistry allow different segments of a single nanowire to be functionalized with different multiple functional groups and/or ligands, giving the wire chemical multifunctionality.

17 Claims, 8 Drawing Sheets

| Ligand | Name | Surface Modified | Proposed Linkage |
|---|---|---|---|
| R-S-H <br> R-S-S-R' | Thiols <br> Disulfides | Au, Ag, Cu <br> Hg, Fe | R-S-▨ |
| R-CN | Cyanides | Pt, Pd | R-CN-▨ |
| $\underset{R-C-O-H}{\overset{O}{\|\|}}$ | Carboxylic Acids | Metal Oxides | $R-C\underset{O-▨}{\overset{O-▨}{\diagdown}}$  $\underset{R-C-O-▨}{\overset{O}{\|\|}}$ |
| $\underset{\underset{O}{\overset{\|\|}{R-P-O-H}}}{}$ | Phosphonates | Metal Oxides | $\underset{\underset{O}{\overset{\|\|}{R-P-O-▨}}}{}$ |
| $\underset{Me}{\overset{Me}{R-Si-O-R}}$ | Siloxanes | Metal Oxides | $\underset{Me}{\overset{Me}{R-Si-O-▨}}$ |
| $\underset{H}{\overset{O}{\overset{\|\|}{R-C-N-O-H}}}$ | Hydroxamic Acids | Metal Oxides | $\underset{H}{\overset{R}{\diagdown}}\underset{N-O-▨}{\overset{C-O-▨}{}}$ |

*Figure 3*

MULTIFUNCTIONAL MAGNETIC NANOWIRES

This application claims priority to U.S. provisional patent application 60/290,338, filed May 14, 2001, and to U.S. provisional patent application 60/336,718, filed Dec. 7, 2001.

BACKGROUND OF THE INVENTION

1. Field of the Invention

The invention generally relates to magnetic nanowires. In particular, the invention provides multisegmented, multifunctional magnetic nanowires for the probing and manipulation of molecules at the cellular and subcellular level.

2. Background of the Invention

The ability to selectively probe and manipulate molecules at the cellular and subcellular level is critical in both basic research and the development of biotechnology applications. One powerful method to do this is to use small particles that interact with specific molecules or individual cells, and which respond to a magnetic field. This approach has found widespread application in cell sorting, biosensing, and studies of mechanical properties of cells using magnetic particles or beads.

For example, particles or beads having magnetic properties have previously been used in separation support systems (see U.S. Pat. Nos. 5,834,121; 5,395,688; 5,356,713; 4,774,265; and 4,554,088, incorporated by reference herein). In particular, magnetically separable support systems have been suggested for the detection of biomolecules by attaching a ligand to a magnetizable bead, attaching a detection molecule to the ligand, permitting the detection molecule to bind to a target molecule, and retrieving the resulting product by use of a magnetic field or other means.

However, a significant limitation of these magnetic carriers is that they have only a single chemical functionality per particle. Further, such magnetic beads or particles have a relatively uniform structure and therefore display relatively uniform magnetic properties.

It would be of benefit to have available magnetic entities which could be used to selectively manipulate and probe molecules at the cellular and subcellular level which contained multiple chemical functionalities per entity. Further, it would be of benefit if the multiple chemical functionalities were spatially resolved from each other. In addition, it would be of benefit if the magnetic properties of such entities could be manipulated and tailored to give the entities a variety of responses to an applied magnetic field.

SUMMARY OF THE INVENTION

It is an object of this invention to provide magnetic nanowires comprising one or more segments in which a molecular functional group or ligand has beenbound to the surface of at least one segment of the wires. The wires are fabricated from materials such as platinum, iron, cobalt, nickel, gold, silver, copper, iron oxide, copper oxide, zinc oxide, and alloys of these materials such as FeCo, NiFe, AuAg, and CuNi. In multisegmented wires, a specific functional group is localized to a particular segment. Examples of such functional groups are thiols, disulfides, amines, cyanides, carboxylic acids, phosphonates, siloxanes, and hydroxamic acids. Further, the wire may comprise ligands associated with the wire, either directly to the wire or via a functional group. In multisegmented wires, the ligands are localized to a particular segment. Examples of ligands include proteins, fibronectin, DNA, RNA, enzymes, ribozymes, hydrophobic materials, hydrophillic materials, saccharides, cells, tissue, microorganisms, bacteria, viruses, and chemoattractants.

The wire or one or more segments of the wire may be formed from a fluorescent or luminescent material, or may have an associated fluorescent label.

In another aspect of the present invention, a method of forming a functionalized magnetic nanowire is provided. The method comprises providing a magnetic nanowire having one or more segments, and associating functional groups or ligands with at least of one said segments. The segments may be formed from a material such as platinum, iron, cobalt, nickel, gold, silver, copper, iron oxide, copper oxide, zinc oxide, and alloys of these materials such as FeCo, NiFe, AuAg, and CuNi. Potential functional groups include non-adhesive compounds, thiols, disulfides, cyanides, carboxylic acids, phosphonates, siloxanes, and hydroxamic acids. Potential ligands include proteins, DNA, RNA, enzymes, ribozymes, hydrophobic materials, hydrophillic materials, saccharides, cells, tissue, microorganisms, bacteria, viruses, fibronectin, and chemoattractants. At least one segment of the wire may be formed from a fluorescent or photoluminescent material, and the nanowire may have an associated photoluminescent label.

The present invention further provides a method of binding a target molecule with a magnetic nanowire. The method comprises contacting the target molecule with the magnetic nanowire. The magnetic nanowire comprises at least one segment associated with a functional group or ligand capable of binding to the target molecule. The functional group or ligand is allowed to bind the target molecule. Potential functional groups are non-adhesive compounds, thiols, disulfides, cyanides, carboxylic acids, phosphonates, siloxanes, and hydroxamic acids. Potential ligands include proteins, fibronectin, DNA, RNA, enzymes, ribozymes, hydrophobic materials, hydrophillic materials, saccharides, cells, tissue, microorganisms, bacteria, viruses, and chemoattractants. The method may further include identification of the target molecule, as well as manipulating or retrieving the nanowire after the target molecule is bound to it.

In yet another aspect, the present invention provides a method of binding a magnetic nanowire to a cell. The method involves contacting the cell with the magnetic nanowire. The magnetic nanowire has associated with it functional groups or ligands capable of binding to the cell. The functional groups or ligands are allowed to to bind to the cell. In one embodiment, the nanowire is assembled into a two- or three dimensional structure.

The present invention further provides a magnetized cell. The magnetized cell comprises a cell, and a magnetic nanowire associated with the cell.

BRIEF DESCRIPTION OF THE DRAWINGS

FIG. 1A depicts magnetic particles embedded in a polymeric matrix functionalized with a single functional group. FIG. 1B depicts multifunctional nanowires with two different organic ligands designated R and R' each bound to a different functional group (S or $CO_2$) to give spatially resolved multifunctional chemical specificity.

FIG. 3 depicts examples of suitable functional groups for use in the practice of the invention.

DETAILED DESCRIPTION OF THE PREFERRED EMBODIMENTS OF THE INVENTION

The present invention provides magnetic nanowires and methods for their use in the selective manipulation and probing of molecules at the cellular and subcellular level. The magnetic nanowires of the present invention provide advantages over previously known magnetic beads and particles in that they may be multiply functionalized. In one embodiment of the invention, the nanowires may be multi-segmented and multifunctional, i.e. multiple, localized functional groups may be present on each wire. This is possible because the different segments of the wire are formed from different materials and are therefore able to selectively bind with the functional groups. Different functional groups are thus attached to different segments of the wire and are spatially resolved from each other along the length of the nanowire. Individual segments of the nanowires may be fabricated so that, in addition to differentially reacting with functional groups, they may also display varying properties. For example, at least one of the segments of the nanowires of the present invention is magnetic but other segments may be nonmagnetic. Further, the magnetic segments may be fabricated so that they display differing degrees and types of magnetism, as is described in detail below. Due to the fact that the wires are magnetic, they may be readily detected and retrieved.

Figure 1A:
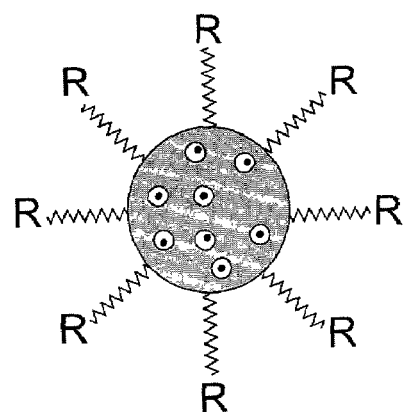
FIGS. 1A and 1B.
Figure 1B:
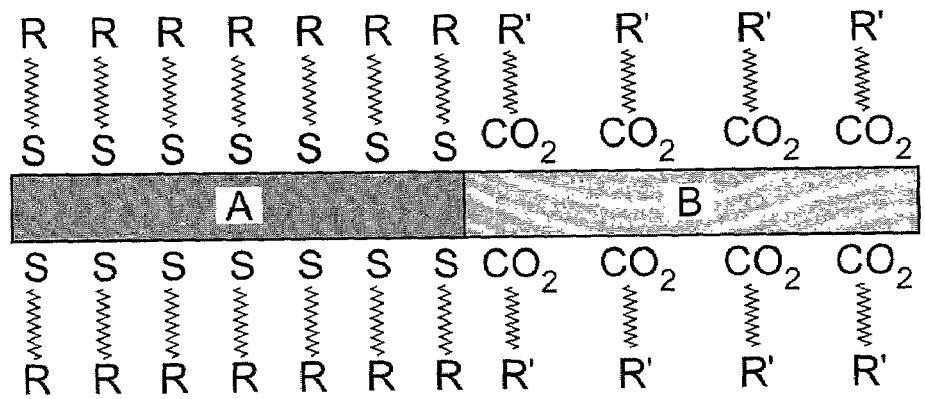

An schematic illustration of the nanowires of the present invention compared to known unifunctionalized magnetic beads is provided in FIGS. 1A and B. FIG. 1A depicts a previously available micron-sized magnetic bead consisting of magnetic particles embedded in a polymer matrix. The bead has a terminal end group, R. In contrast, FIG. 1B depicts an exemplary nanowire in accordance with one embodiment of the invention. The multifunctional exemplary nanowire depicted in FIG. 1B has two segments designated as A and B. In this example, A represents a non-magnetic noble metal (e.g., Au) while B represents a magnetic metal (e.g., Fe or Ni). Segment A is functionalized with functional group S (thiol) which is bound to terminal end group R. However, segment B is functionalized with different functional group $CO_2$ (carboxylate) which is bound to different terminal end group R'.

Those of skill in the art will recognize that the nanowires of the present invention may be formed from a variety of suitable materials. Such materials include, but are not limited to metals such as platinum, iron, cobalt, nickel, gold, silver, copper, either in pure or alloyed form, or compounds such as iron oxide or the semiconductors copper oxide and zinc oxide. In a preferred embodiment of the instant invention, the magnetic segments of nanowires are fabricated of ferromagnetic materials such as Co or Ni. The nanowires may be comprised solely of magnetic materials, or of a mixture of magnetic and nonmagnetic materials. Those of skill in the art will recognize that the nanowires of the present invention may be fabricated from any suitable material so long as the resulting nanowires can be utilized in the practice of the present invention. Examples of such materials and their relevant properties are given in Table 1.

TABLE 1

| Material | Properties |
| --- | --- |
| Fe, Co, Ni | ferromagnetic, various ligands bind to air formed oxides |
| $Fe_3O_4$ | ferromagnetic (high spin polarization) |
| Au, Ag, Cu | non-magnetic, strong binding with thiols |
| Pt | non-magnetic, strong binding with isocyanides |
| $Cu_2O$ | p-type semiconductor, visible luminescence |
| ZnO | n-type semiconductor, visible and UV luminescence |

The nanowires of the present invention are quasi-one-dimensional entities with large aspect ratios. In a preferred embodiment of the present invention, the diameter of a nanowire is in the range of about 10–300 nanometers, and the length of the nanowire is from 10 nm to tens of microns. However, those of skill in the art will recognize that the preferred dimensions of a nanowire will vary from application to application, and that the dimensions of a nanowire can be adjusted during fabrication so as to be of a length suitable for a particular application.

Nanowires may be fabricated by any suitable method known in the art. In one embodiment of the invention, nanowires are fabricated by electrodeposition of the substrate into nanoporous templates. [1–12]. This approach offers several advantages, including the ability to fabricate large numbers of nanowires, and to introduce composition modulation along the length of the wires. The template material maintains the nanowires within its thickness, and the nanowires are usually perpendicular to the plane of the template. By using templates with many, parallel-walled nanopores, arrays of nanowires can be grown with wire diameters from a few nanometers up to tens of microns, wire lengths up to 100 μm, and areal densities up to $10^9$ $cm^{-2}$ (limited by wire diameter). However, since many essential characteristics of the nanowires, such as shape, size, and surface roughness, directly reflect the properties of the pores, templates with well-controlled pore morphology are crucial for nanowire fabrication by this tehcnique. Examples of templates include polycarbonate membranes or mica films containing etched nuclear particle tracks [13–17], porous alumina films formed by anodic oxidation of aluminum [18–20], and nanochannel glass films [21].

In fabricating nanowires by electrodeposition, one side of the porous template is usually coated with a metal layer, which serves as a working electrode in a three-electrode deposition cell. The deposition takes place inside the nanopores, starting from the metal layer. Multisegmented nanowires are made by either sequentially changing the deposition solution, or from single multi-reagent solutions by varying the deposition potential.

To create suspensions of nanowires, the nanowires are first removed from the template by dissolving the template material. For example, polycarbonate is dissolved in chloroform, alumina is dissolved in warm potassium hydroxide, and mica is dissolved in hydrofluoric acid. After suitable cleaning, the wires may be suspended in a variety of solvents by ultrasonic agitation.

The magnetic properties of a nanowire, or of individual segments of a nanowire, can be "tuned". By "tuning" we mean that the composition or morphology of the wire can be adjusted to vary the magnetic behavior of the wire, for example by controlling the strength, existence, or orientation of its permanent magnetic moment, to change the way it responds to a magnetic field. The tuning of the wire is accomplished by precisely varying parameters such as the size, shape, and composition of the segments. For example, wires may be fabricated via the alternating deposition of two or more different magnetic materials along the length of the wire. In addition, the magnetic properties of the wire may be further modified by the introduction of non-magnetic segments.

Nanowires may also be "tuned" by introducing alterations in their morphology. Nanowires with long magnetic segments form single-domain ferromagnetic states with large coercive fields ($H_c \approx 40$ kA/m (500 Oersteads) for Ni) due to their magnetic shape anisotropy. Based on the bulk saturation magnetization, $M_s \approx 1.7 \times 10^6$ A/m (1700 Oe) for Fe and $M_s \approx 5 \times 10^5$ A/m (500 Oe) for Ni, a typical nanowire with length L=10 μm, and diameter d=100 nm will have a magnetic moment $\mu \approx 1.4 \times 10^{-13}$ Am$^2$ for Fe, and $\mu \approx 4 \times 10^{-}$Am$^2$ for Ni independent of the applied field. This is comparable to the typical saturated magnetic moment $\mu_s$ for magnetic beads and thus similar forces may be applied at high fields to the nanowires as to the beads. However, since beads are superparamagnetic, they achieve $\mu_s$ in fields H exceeding $10^5$ A/m (1.25 kOe). Thus, at low fields, larger forces can be applied to the nanowires of the present invention than to magnetic beads For example, nanowires can be constructed that have low moments in small fields. These wires are useful, for example, in applications in which it is desirable to minimize inter-wire interactions that can lead to aggregation. This is done with wires with disk-shaped magnetic segments by exploiting interlayer magnetic coupling across non-magnetic spacer segments [22]. By appropriately choosing the spacer's thickness, this coupling is antiferromagnetic, and the resulting anti-parallel alignment of the segments produces wires with no net moment in zero field. Above a threshold field, this coupling is overwhelmed, and the segments' moments align, giving the wire a net moment and producing a corresponding force on it due to the action of the field on this magnetic moment. By varying the spacer thickness, the interlayer coupling strength can be varied, and the threshold field for the application of a force to different nanowires can be tuned (see e.g. FIG. 7). This permits the development of multicomponent nanowires with tunable threshold fields.

Figure 2:
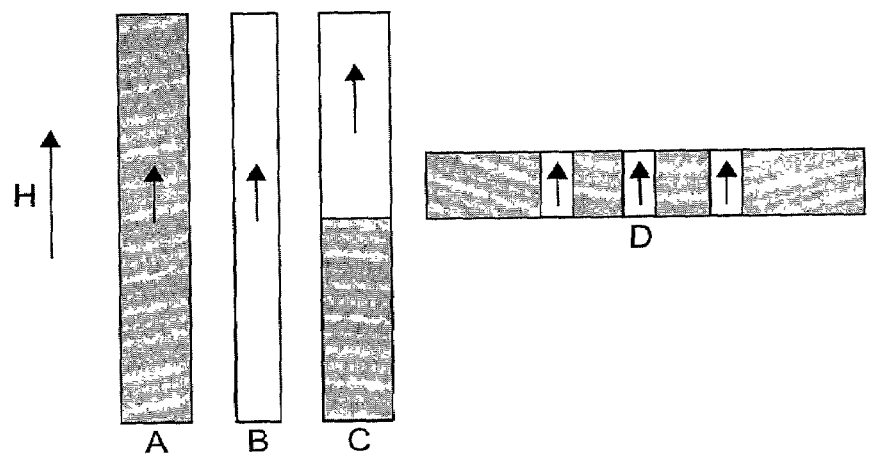
FIG. 2 depicts the tuning of the magnetic moment of an exemplary nanowire.

Thus, by combining different deposition strategies, it is possible to create a wide variety of nanowires, each of which is tuned or tailored to possess desired behavior in response to magnetic fields. Any number or combination of magnetic or non-magnetic segments arranged in any desired pattern may form a nanowire in accordance with embodiments of the invention. FIG. 2 schematically depicts the tuning of the magnetic moment of exemplary nanowires. In the FIG. 2, Wire (a) has a larger magnetic moment than Wire (b) even though they are the same length. In contrast, Wire (c) retains the same dimensions as Wire (a) but has a smaller magnetic moment due to the introduction of a non-magnetic segment. In Wire (d), the introduction of disk-shaped magnetic segments which are short compared to their diameter makes the wire align with its long axis perpendicular to a magnetic field. In all cases, (a)–(d), the same material may be used. This is due to magnetic shape anisotropy that makes the magnetic moment of a disk preferentially lie in the plane of the disk, perpendicular to the axis of the wire. When the disks' moments align parallel to the field, the wire rotates to be perpendicular to the field.

In accordance with one embodiment, the nanowires of the present invention may be modified with functional groups. The functional groups may be atoms or groups of atoms that are capable of further chemical reactivity such as reacting with a ligand to attach the ligand to the wire, or to bind a target molecule. Further, different segments of the same nanowire may be functionalized with different functional groups, providing multiple discrete functional regions that are spatially resolved along the length of the wire. For example, a first segment of a nanowire may comprise a metal oxide or a metal with a native oxide layer whose surface can be functionalized with a functional group such as a carboxylic acid group. A second segment of the nanowire may comprise a non-magnetic substrate, such as gold, which can be functionalized with a thiol group. Thus, an exemplary two segment nanowire may be functionalized with two independent functional groups wherein each functional group may have different chemical properties. Examples of functional groups that may be used in accordance with alternative embodiments of the invention are set forth in FIG. 3.

Such functional groups may be capable of interacting directly with a molecule or cell of interest in the methods of the present invention. However, the functional group may serve to link or attach to the nanowire a secondary molecule or ligand that is capable of interacting with a molecule or cell of interest in the methods of the present invention. The term "ligand" refers to any entity capable of specifically or non-specifically binding to, attracting, localizing in proximity to, or detecting the presence of a target molecule. The term "target molecule" refers to any molecule capable of specifically or non-specifically binding to a ligand. In a preferred embodiment of the present invention, different ligands are linked to different segments of the nanowire. For example, a first ligand (e.g. an antibody specific for a protein A) may be linked to a first segment of the nanowire, and a second ligand (e.g. an antibody specific for a protein B) may be linked to a second segment of the nanowire.

In the process of linking a ligand to a nanowire via a functional group, the functional group may be first attached to the nanowire, and then the nanowire may be reacted with the ligand to tether the ligand to the nanowire. Alternatively, the ligand itself may be derivatized so as to contain a functional group suitable for linking it directly to a wire. In fact, some suitable secondary molecules may inherently possess a "functional group" (e.g. the sulfhydryl groups of cysteine residues, and the carboxy- and amino-terminal functional groups of polypeptides) that are suitable for directly reacting with a segment of a wire.

Other molecular groups may also be included in the linking arrangement. For example, linear or branched alkyl chains or other polymers may be introduced between the wire and a ligand in order to, for example, position the ligand further from the surface of the wire, or to offer the possibility of introducing more than one ligand per functional group to order to increase ligand density on the wire. Those of skill in the art will recognize that there are many strategies for attaching a useful ligands to the magnetic nanowires of the present invention. All such variations and modifications are intended to be encompassed by the present invention. A "functionalized nanowire" is one which has been modified to contain a moiety which is added to the wire after fabrication, for example, a functional group such as a thiol, or a linking molecule such as an alkyl chain, or a ligand.

Examples of ligands which are suitable for use in the practice of the present invention include, but are not limited to, molecules and macromolecules such as proteins and fragments of proteins, peptides and polypeptides, antibodies, receptors, enzymes, substrates, substrate analogs, ribozymes, structural proteins, nucleic acids such as DNA and RNA and DNA/RNA hybrids, saccharides, lipids, various hydrophobic or hydrophillic substances, lipophilic materials, chemoattractants, enzymes, hormones, fibronectin. and the like. Further, such molecules and macromolecules may be naturally occurring or synthetic in nature. The term ligand may also include larger entities such as cells, tissues, entire microorganisms, viruses, etc.

Those of skill in the art will recognize that, in many circumstances, the terms "ligand" and "target molecule" are not absolute and may be interchanged, i.e. a molecule that is described as a ligand in one circumstance may be described as a target molecule in another circumstance.

In a preferred embodiment of the present invention, a single type of ligand is associated with a segment of a nanowire. However, those of skill in the art will recognize that this need not be the case. For example, it may be desirable to associate two (or more) ligands with a single segment of a nanowire in order to achieve a desired result. In the practice of the present invention, ligands may be arranged on the segments of a nanowire in any desired combination or configuration. The segmented nature of the nanowires allows the orderly positioning of ligands via functional groups at defined positions along the wire.

The attachment or association of a functional group or ligand to the wire, or of a ligand to the wire, and of a ligand to a target molecule may be of any suitable nature. For example, they may be associated via magnetic, covalent, ionic, electrostatic, hydrophobic or hydrophillic interactions or attractions.

In another embodiment of the invention, magnetic manipulation of the nanowires is combined with the well-developed and powerful optical tracking techniques currently in use in biological and other systems. For example, fluorescent or photoluminescent materials may be associated with the nanowires, either by direct incorporation into the nanowire during fabrication, or by attachment to the nanowire after fabrication. For example, zinc oxide or ZnO, can be electrochemically deposited to form photoluminescent nanowire segments. Alternatively, cuprous oxide, $Cu_2O$ can be used to form photoluminescent nanowires which absorb light in the visible region and emit light in the near infrared or IR region, a spectroscopic region useful for many biological applications. Thus, in accordance with one embodiment of the present invention, a variety of photoluminescent materials can be electrodeposited in compositionally modified nanowires to yield materials that have both luminescent and magnetic segments.

Alternatively, luminescent chromophores may be bound to nanowires after fabrication. The chromophores may be bound directly to specific segments of a nanowire, (e.g. the chromphores may be capable of reacting with specific segments of the wire, for example, via a functional group). Alternatively, for some purposes it may be desirable to tag nanowires nonspecifically. In yet another embodiment of the invention, the chromophore may not be attached directly to the wire, but rather to a ligand or to a linking molecule (e.g. an alkyl chain or other polymeric chain) so that the chromophore is positioned away from the surface of the wire. A wide variety of luminescent chromophores with appropriate chemical compositions are known and commercially available, and the relevant methods of detection are well known to those of skill in the art. For example, see the World Wide Web site of Molecular Probes.

Because the multifunctional nanowires of the present invention are magnetic, they can readily be manipulated and/or retrieved by straightforward methods which are well-known to those of skill in the art, such as the application of magnetic fields. Examples include but are not limited to the application of a non-uniform magnetic field. This may be accomplished with, for example, external magnets or magnetic tweezers, or with more localized field sources such as lithographically patterned magnetic structures, microfabricated circuits, or even with other nanowires. Further, the location of magnetic nanowires may also be readily detected and monitored by methods which are well-known to those of skill in the art, including via visual observation. Further, if the wires have been functionalized with a fluorescent tag or label, spectroscopically based detection means can also be employed.

Multifunctional magnetic nanowires have many potential applications in biological systems. Most basically, because the wires are multifunctional, they may be utilized in any system in which it is desirable to utilize a substrate capable of presenting multiple ligands, and/or in which it would be desirable to have the ability to orient and/or retrieve the substrate after the ligand has bound to a target molecule, or to magnetically detect the location of the substrate after the ligand has bound to a target molecule.

For example, the multifunctional nanowires may be utilized to simultaneously bind and detect a plurality of target molecules in a biological sample, the number being limited only by the number of differentially functionalized segments on the wire. Examples of target molecules which can be detected in this manner include but are not limited to proteins and peptides, nucleic acids, lipids and saccharides. Any molecule or macromolecule capable of being bound by a ligand that can be attached to a magnetic nanowire of the present invention may be detected by the practice of the methods of the present invention. Further, the binding may be either specific or non-specific.

Those of skill in the art will recognize that there are many applications for such a tool. For example, the wires may be utilized to simultaneously detect the presence of or to measure multiple compounds present in biological samples such as blood, plasma, urine, semen, saliva, stool samples, swabs (vaginal, oral, etc.), cells (such as mammalian and plant cells), cellular or subcellular extracts, viruses, water samples, and the like. Target molecules that may be detected included drugs, hormones, proteins (e.g. antibodies, antigens, enzymes, etc.), peptides, nucleic acids (e.g. DNA and RNA), carbohydrates, metals, pollutants, and the like. Further, such a tool may be utilized in various assay systems such as for assays of enzymes and substrates (e.g. fluorescence and radio immunoasays) and in nucleic acid hybridization assays.

In addition, the magnetic nanowires may be used for affinity purification of target molecules. For example, one member of a ligand-target molecule binding pair (e.g. antibody/antigen, enzyme/substrate, ligand-receptor, and the like) may be attached to the wire in order to sequester and remove the other member of the binding pair from a sample. The multifunctionality of the nanowires of the present invention is a boon in this application since more than one target molecule can be sequestered and retrieved. This aspect of the invention may be used to obtain desired molecules from a mixture, or to remove unwanted molecule from a mixture e.g. to remove unwanted protein components from antisera or clinical samples, to sequester or remove anti-self antibodies. Because the substances which are bound to the wires are held in place by the wires, the substances may be conveniently washed to remove extraneous matter, and/or transferred to a desired location (e.g. to an assay container).

The target molecule need not be free in solution but may be attached to or embedded in a biological structure such as a cell, subcellular organelle or tissue. Thus, one segment of a functionalized nanowire may serve to target the entire wire to a cell.

Potential applications for this aspect of the invention include but are not limited to: the detection of cell surface receptors; localization/bifunctional capture of multiple cells; transport of a ligand of interest to a targeted cell via binding of a ligand on the wire to a target molecule on the cell surface; study of the motion of cells with associated nanowires; determining abundance of the cells with bound wires by measuring the local field created by the wires; retrieval and thus separation of cells with bound nanowires, including selection of desired cell types or purging of unwanted cell types (because the cells which are bound to the wires are held in place by the wires, they may be conveniently washed to remove extraneous matter and transferred to a desired location); application of a magnetic field to a cell-bound wire to twist the wire and damage or kill the cell; application of an electric current to disrupt the transmembrane potential of the cell, therefore permeabilizing the cell membrane in order to introduce other molecules (e.g. nucleic acids) into the cell; use of a strong current to kill the targeted cell;

In another embodiment, with bi-functionalized wires, one functional group could be used to localize wires to specific anatomical structures inside a cell, and a second to, for example, probe the presence of a relevant protein at that location, sample internal cell compartments, to assess the mechanical and Theological properties of sub-cellular species, or to deliver a substance of interest to that location. Alternatively, if a segment of a nanowire is functionalized with a non-adhesive substance that prevents binding of that segment to a cell, such as ethylene glycol, and the remaining segment with a ligand for a cell-surface receptor, then cells will be able to bind only part of the nanowire. The unbound segment would prevent internalization of these wires; thus, the wires of the present invention would then be permanently held on the outside of the cell surface.

In another embodiment of the invention, nanowires can be made into artificial, magnetic antibodies by functionalizing one segment with a ligand to bind to a specified target molecule, and the other end with a ligand that acts as a beacon to attract immune cells. In this manner, the wires may be used to present stimulartory or co-stimulatory signal to T-cells which induce clonal expansion of T cells.

The location of magnetic nanowires may be detected, either directly by detecting the magnetic fields of the wires, or by detection of a labeled (e.g fluorescent, or photoluminescent) segment of the wire. Luminescent and fluorescent and other optically active materials may be used, for examples, to fabricate nanowires with unique "optical barcoding" for the simultaneous tracking of multiple biological targets. For example, a unique combination of fluorescent and non-fluorescent nanowire segments can be fabricated and assigned a particular optical pattern or bar-code to distinguish the nanowire from other nanowires within a biological or other system. A unique optical pattern or barcode can be applied to a segment of a nanowire functionalized with a particular ligand or designed to bind to a particular target molecule or target molecules. When the nanowire encoded with an optical pattern or barcode is introduced into a biological or other system, it can be located and tracked using a variety of magnetic or optical detection devices. For example, a magnetic nanowire bound to a cell can be used to track the movement of a cell in a biological fluid (e.g., blood, serum, lymph, semen, vaginal fluid).

In another embodiment of the invention, a particular cell or cell type can be optically or magnetically "tagged" with a nanowire. The movement of the cell-bound exemplary nanowire can then be tracked within a fluid system (e.g., the body of a human, animal or plant).

In another embodiment of the invention, nanowires are used as biosensors to detect the presence of and quantitate target molecules. There are many potential applications that use microfabricated magnetic field probes to detect the presence and location of small magnetic entities. For example, cells or molecules bound to nanowires with magnetic segments can be selectively bound to specific regions of a surface. By measuring the local fields produced by the magnetic entities in those regions, the location and/or abundance of the cells or molecules of interest can be determined. Alternatively, motion of individual cells with magnetic entities bound to them can be detected by local field probes. Detection of magnetic nanowires with local field probes is yet another alternative to the optical tracking and detection mechanisms described above. Microfabricated field probes can also provide a means to link biological systems to integrated circuit technology In another embodiment of the invention, tunable magnetic properties and chemical multifunctionality of nanowires are combined in a variety of ways to form one-, two- and three-dimensional nanoscale structures. Multisegmented magnetic nanowires can be manipulated in an external magnetic field to form such structures by taking advantage of the multifunctionality of the nanowires. One strategy is to use one segment of the nanowire as a binding site for a ligand that will also bind to a corresponding segment in another nanowire. For example, short-chain dithiols can be used to link gold segments in multicomponent nanowires. In one embodiment of the invention, controlled assembly of individual nanowires can be induced by functionalizing the non-linking segments of the nanowires with charged tail groups. The electrostatic forces between these segments can be used to control the angle at which two nanowires are attached. This approach can be used to produce ordered and disordered arrays with different dimensionality depending on the functionalization of the wires. Further control can be achieved by combining electrostatic and magnetic interactions. The electrostatic forces between two nanowires with charged monolayers can be significantly larger than the magnetic forces between the same wires. However, the range of the electrostatic interactions can be tuned by changing the ion concentration, which controls the screening length. Complex arrangements of nanowires can thus be achieved by using the long-range magnetic forces to bring wires into proximity. The precise nature of the interactions of the nanowires can be determined by the distribution of the charged segments on the wires.

This approach is of interest, for example, for tissue engineering and in the design of self-healing structures. For example, nanowire structures may function as scaffoldings or templates for cell growth or for the implantation of cells. A cell of interest (for example, a cardiac cell) may be attached to and/or grown on single nanowires. The attachment may be specific (e.g. via a ligand on the wire binding to a target molecule on the cell), or non-specific by introducing nanowires into a cell culture substrate (e.g. culturing the nanowires with the cells and allowing the cells to grow on the wires). Alternatively, the nanowires may be assembled into the desired structure prior to the attachment of the cells, and the cells allowed to attach to and grow on the structure. The open nature of these exemplary structures will allow easy diffusion of nutrients through the assembled nanowire network. As such, the structures will provide superior substrates for, for example, the culture of cells compared to typical two-dimensional culturing techniques (e.g. on the flat surface of a Petri dish). The structures can provide scaffolding for cells grown in liquid culture. It is well known that cells (e.g. cardiac cells) grown on supportive three-dimensional scaffolding such as threads of suture material exhibit characteristics more like that of heart tissue than those grown on flat surfaces. The nanowires of the present invention provide such supportive scaffolding with the added benefit of ready manipulation and retrieval of the structures, and the ability to monitor the location of the structures, if desired.

In one embodiment of the present invention, such structures with attached cells could be used in the transplantation of cultured cells into a an organism of interest. For example, tissue which had been cultured in vitro could be introduced into an organism.

EXAMPLES

Methods

Nickel Nanowire Fabrication. Nickel nanowires were fabricated by electrochemical deposition into commercially available 50 μm thick alumina filter templates (Anodisck, Whatman, Inc.) with a nominal minimum pore diameter of 100 nm. A gold film was sputter-deposited on one side of the template to serve as a working electrode. Nickel was deposited from a solution of 20 g $L^{-1}$ $NiCl_2.6H_2O$, 515 g $L^{-1}$ $Ni(H_2NSO_3)_2.4H_2O$, and 20 g $L^{-1}$ $H_3BO_3$, buffered to pH 3.4 at a potential of −1.0 V (Ag/AgCl). The wires were grown to be 5–25 μm in length as controlled by the deposition time. The nanowires' average radius was a=0.18 ±0.02 μm, as determined by scanning electron microscopy. The wires are therefore nanometers in diameter and microns in length. The nanowires were removed from the templates by dissolving the alumina in 0.5 M KOH at T=50° C. for 24 h, stirring occasionally. The wires were collected by entrifuging at 7000 rpm for 10 min, or by placing a small magnet on the side of the flask. This latter magnetic collection procedure exposed the wires to a field in excess of 1 kG and permanently magnetized the wires with their magnetic moments parallel to their long axis. With both procedures, the supernatant was decanted and the wires were resuspended by sonication in 1.5 mL of absolute ethanol. This collection and rinsing procedure was repeated twice with fresh ethanol or other solvents of interest and the supernatant was generally stored in these solvents in air. Aggregation and settling of the wires was observed under a variety of conditions, and brief sonication (~5 s, 42 kHz, Cole-Parmer model 8890) consistently resulted in redispersion of the wires, regardless of their remnant magnetization.

Nanowires suspended in low viscosity liquids such as water, ethanol, and 2-propanol precipitate from the solutions in the course of several minutes. In addition, aggregation occurs due to interwire magnetic forces. To minimize aggregation and precipitation, the nanowires were suspended in more viscous media such as 1:1 hexadecane ($C_{16}H_{34}$)/octadecane ($C_{18}H_{38}$) mixtures or ethylene glycol in order to increase stability. For example, in hexadecane/octadecane the nanowires remain suspended for period of days.

Gold-Nickel Nanowire Fabrication To make Au—Ni nanowires, Ni segments were grown as described above. The Ni solution was then removed from the deposition cell and replaced with a commercially available Au-plating solution (Technic 495). Further electrodeposition resulted in Au segments growing on the Ni segments to form two-segment nanowires.

Functionalization of Nanowires with Porphyrin. To functionalize magnetic nanowires with fluorescent porphyrins, Hematoporphyrin IX, [8, 13-bis(1-hydroxyethyl)-3,7,12,17-tetramethyl-21H, 23H-porphine-2,18-dipropionic acid] was employed. Hematoporphyrin IX has two intense, red fluorescence bands ($\lambda_{max}$=626 and 696 nm in ethanol) and two carboxylic acid groups that are known to bind strongly to metal oxides and to the native oxide films on metals, such as nickel. Approximately one million 10 μm-long Ni nanowires were fabricated as described, placed in 20 mL of a 10 mM hematoporphyrin IX ethanol solution, and allowed to react at room temperature for 1 hour. The wires were then collected by placing a magnet outside of the reaction flask, the solution was decanted, and the wires were rinsed with excess ethanol until no fluorescence was observed from the supernatant solution. Typically, between two and four iterations were required before the supernatant was nonemissive. The wires were then re-suspended in a 1:1 hexadecane-octadecane solution.

Cell Culture. HeLa human epithelial cells were cultured in Dulbecco's modified Eagles' medium (DMEM) containing Na-pyruvate and L-glutamine as supplied, supplemented with 5% fetal bovine serum. NIH-3T3 mouse fibroblast cell were cultured in DMEM as above, supplemented with 5% calf serum and 1% penicillin/streptomycin.

Attachment of Nanowires to Cells. Cells grown on either glass coverslips or on plastic culture dishes were exposed to solutions of functionalized nanowires (approximately $10^6$ nanowires per ml). The nanowires are allowed to settle on the cells, and the cell/nanowire mixture is then incubated for periods of one to twelve hours. Wires that do not bind to the cells may be washed away by gentle rinsing.

Example 1

Fabrication of Fluorescent Nanowires

Porphyrins are an important class of macrocycles that regulate many biological processes such as the transport and activation of dioxygen. Free-base porphyrins display intense fluorescence and are readily derivatized with functional groups that bind tenaciously to solid-state surfaces, but do not affect the fluorescent properties.

Figure 4:
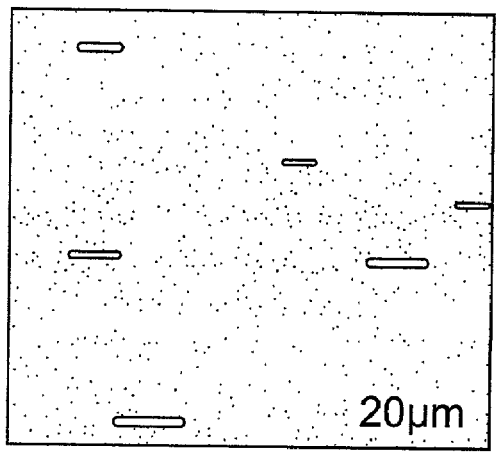
FIG. 4. Fluorescent image of Ni nanowires functionalized with hemato-porphyrin IX. The nanowires are suspended in a hexadecane-octane mixture and aligned in an 8 Gauss magnetic field.

Nickel nanowires were reacted with hematoporphyrin IX as described. Flouuresence images of the wires after reaction (see FIG. 4) demonstrate that the nickel wires display the characteristic fluorescence of hematoporphyrin IX, while the solution itself is non-fluorescent. Control experiments with porphyrins lacking terminal functional groups did not bind to the wires under the same conditions (data not shown). The control experiment suggests that binding occurs through the carboxylic acid groups on the hematoporphyrin IX to the native oxide film on the nickel surface. This experiment demonstrates that the hematoporphyrin IX binds to nickel nanowires and that nanowires with bound hematoporphyrin IX may be readily visualized.

Example 2

Selective Functionalization of Two-Component Nanowires

Approximately one million 12 µm-long, two-component Au—Ni nanowires were fabricated as described in Methods. The wires were comprised of an 8 µm Au segment and a 4 µm Ni segment. The wires were placed in a 20 mL ethanol solution containing 20 mM octane thiol (capable of interacting with Au) and 10 mM hematoporphyrin IX (capable of interacting with the oxide film of the Ni portion of the wire). The wires were allowed to react at room temperature for 1 hour. The wires were then collected by placing a magnetic stir bar outside of the reaction flask and decanting the solution. The wires were then rinsed with excess ethanol and isolated on silicon substrates.

Figure 5A:
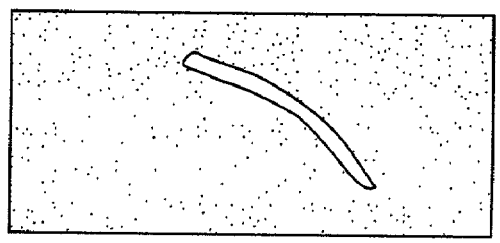
FIGS. 5A and 5B. A, visible light and B, fluorescence images of a 12 μm-long Au/Ni nanowire. The 8 μm Au segment is functionalized with octanethiol, and the 4 μm Ni segment with fluorescent hematoporphyrin IX.

FIGS. 5A and B shows visible light (A) and fluorescence (B) images of the wires after functionalization. As can be seen by comparing the two images, the porphyrin-terminated nickel component of the wire is fluorescent while the thiol-terminated gold is not. This example demonstrates a species of interest (e.g. a fluorescent label) can be selectively placed on one segment of a multisegmented nanowire.

Example 3

Interaction Between Nanowires and Cells

Figure 5B:
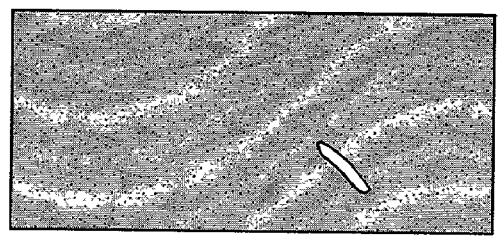
Figure 6:
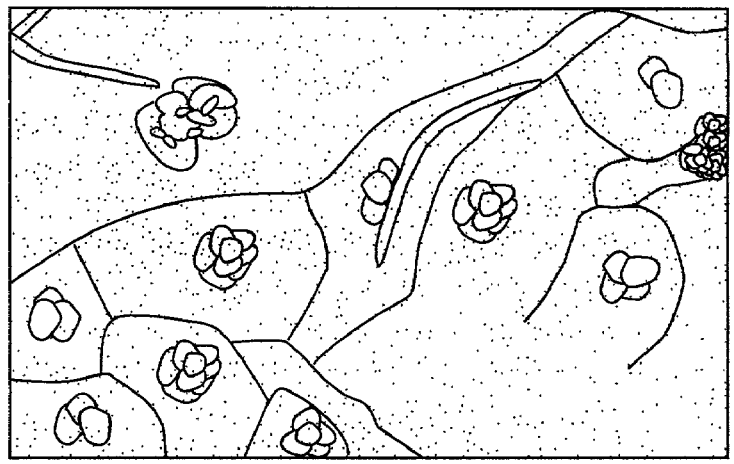
FIG. 6. HeLa cell elongates asymetrically to conform to a bound, 40 μm long Ni wire.

Experiments were conducted in which the tendancy of magnetic nanowires to adhere to living cells was investigated. HeLa cells were exposed to bare Ni wires, or to Ni wires that had been coated with either 11-aminoundecanoic acid or rat-tail collagen. Typical results are depicted in FIGS. 5 and 6. The amine termination of 11-aminoundecanoic acid has a general, non-specific affinity for cells, and rat-tail collagen is known in the art to promote cell-surface adhesion.

Bare Ni wires showed no tendency to adhere to the HeLa cells (not shown). However, as can be seen, both the 11-Aminoundecanoic acid and collagen coated wires adhered strongly to the cells. In fact, the cells displayed a tendency to internalize the wires. An important observation was that the wires do not appear to be toxic to the cells. The strong adherence of the nanowires to the cells was confirmed by the manipulation of the cells with bound wires using magnetic fields. For example, cells with a bound magnetic wire were rotated in place by the torque produced on the nanowire's magnetic moment by an external magnetic field (FIG. 5).

Figure 7A:
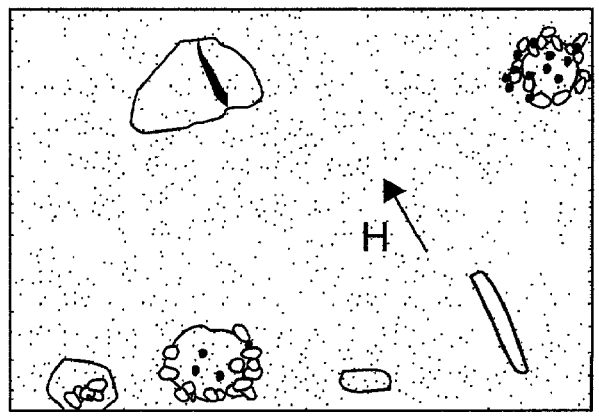
FIGS. 7A and 7B. Control of orientation of HeLa cells via a bound 12 μm long magnetic Ni nanowire. Both a cell with a bound wire (upper left) and a free nanowire (lower right) rotate to keep the nanowires' magnetic moments parallel to the applied field H.
Figure 7B:
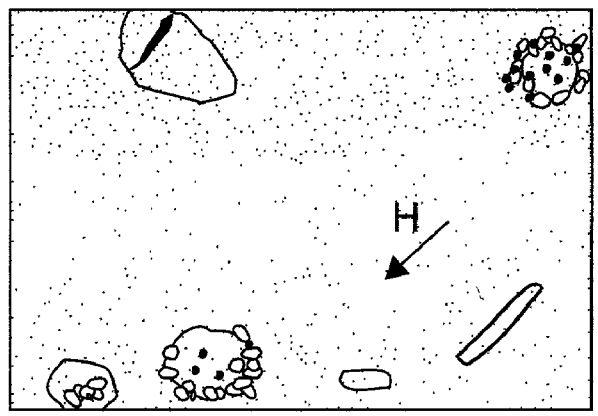

Further observations showed that the binding of a nanowire to a cell influences the cell's orientation on a substrate. As cells with a bound nanowire spread on a flat surface, they did so asymmetrically with their long axis parallel to the bound nanowire, as shown in FIGS. 7A and B.

This example demonstrates that while bare nanowires did not attach to living cells, nanowires coated with substances known to promote adhesion to cells did so. In some cases, the nanowires were internalized by the cells, yet the wires were non-toxic. Further, the position of the cells with bound nanowires could be manipulated using an external magnetic field.

Example 4

Alignment and Self-Assembly of Nanowires.

Fluorescent and non-fluorescent nanowires functionalized with fluorescent porphyrins and suspended in fluid solution can be oriented and assembled with magnetic fields. Self-assembly of the nanowires from suspension is achieved by allowing the wires to settle onto flat, glass substrates. The magnetized nanowires interact with each other through dipolar forces, and tend to aggregate. This occurs both during settling and on the substrates, where they remain mobile for periods of up to hours. If the nanowires are initially randomly oriented in the fluid, then this process yields random collections of nanowires, due to the dependence of the dipolar interaction between pairs of nanowires on their relative orientation. However, controlled assembly may be achieved by applying a small external field H <10 G. By pre-aligning the suspended nanowires, this field suppresses the tendency towards random aggregation, and leads to the formation of extended head-to-tail nanowire chains. These chains can become quite long, ultimately extending over hundreds of microns on the substrates.

Figure 8A:
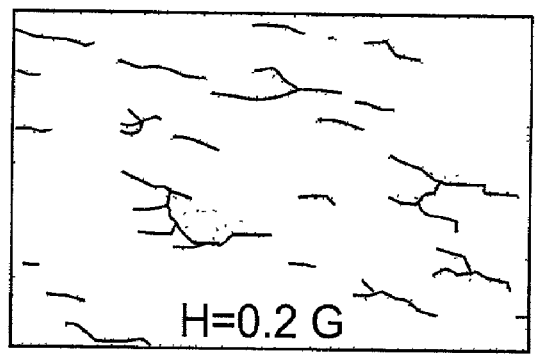
FIG. 8A-C. Optical micrographs of Ni nanowire chain formation after precipitation from a water suspension in external magnetic fields of A, H<0.2 G; B, H=2 G; and C, H=8G.
Figure 8B:
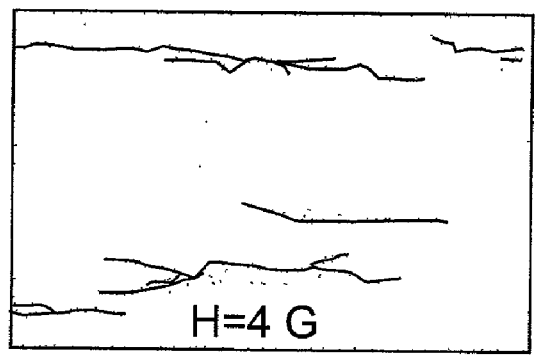
Figure 8C:
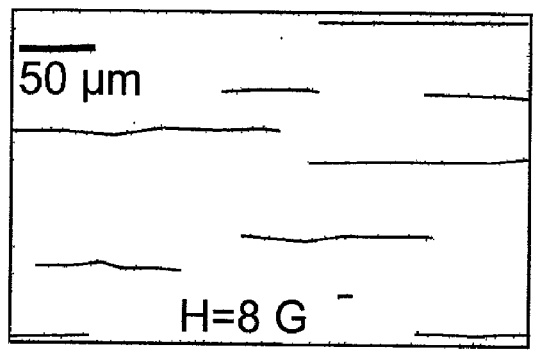

The morphology of the chains is governed by the external field strength. As illustrated in FIG. 8A-C, for Ni nanowires, at higher fields the chains become progressively straighter (FIG. 8C) and the tendency to form multiple branches seen in FIGS. 8A and 8B is eliminated. These chains are stable when the field is removed, and retain their shape when the solvent is evaporated slowly.

Experiments on chain formation with three component nanowires, with non-magnetic Au ends and a central magnetic Ni segment, were also carried out The results showed that the three component nanowires form overlapping chains so as to bring the ends of the magnetic segments of adjacent wires in the closest possible proximity (data not shown).

This example demonstrates that self-assembled structures of nanowires with controlled morphology may be formed and has application in providing scaffolds for tissue engineering.

Example 5

Dynamics of Chain Formation.

Figure 9A:
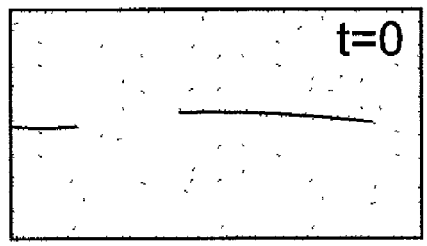
FIGS. 9A and 9B. A, video microscopy images showing attractive interaction between two Ni nanowire chains in ethylene glycol, coaligned in a 4 Oe external field. B, Separation vs time for four chain-formation events in 4 Oe external field. Events (1) and (2) were in water, and events (3) and (4) were in ethylene glycol. Large circles (a)–(d) on curve (3) correspond to the four panels in A.
Figure 9B:
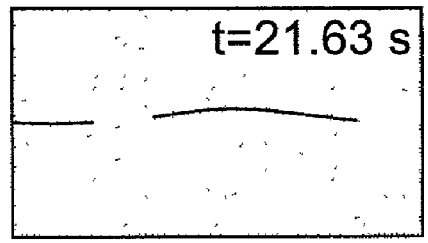
Figure 9C:
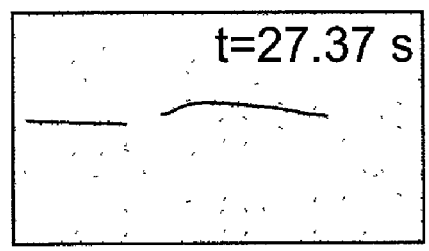
Figure 9D:
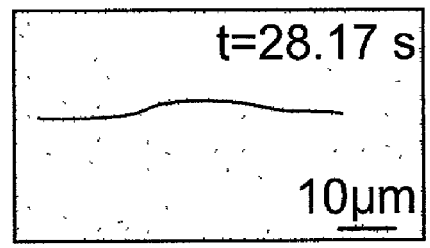
Figure 9E:
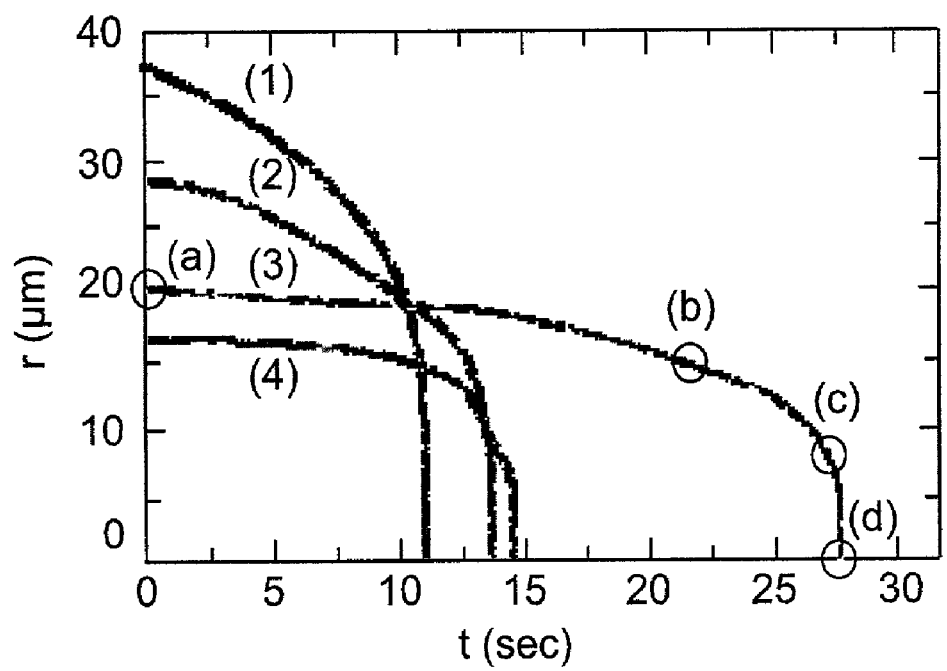

The dynamics of chain formation were studied via video microscopy. FIG. 9A shows four video frames (a–d) from the joining of two short chains composed of two and three nanowires, respectively, carried out in ethylene glycol at T=20° C. and H=4 G. From these data, the chains' locations can be determined for each frame, and the end-to-end separation vs. time r(t) for the event in FIG. 9A is shown in as Trace 3 in FIG. 9B. The large circles indicate the data points corresponding to the frames in FIG. 9A. FIG. 9B also shows data for a second event in ethylene glycol (Trace 4), along with two events observed in water at T=35° C. (Traces 1 and 2). The separation vs time curves are qualitatively similar for all joining events, but the significantly higher viscosity of ethylene glycol results in a much slower motion.

The force F between both single nanowires and nanowire chains can be modeled very accurately by treating them as extended magnetic dipoles. Their hydrodynamics is dominated by viscous drag effects, and hence a wire or chain's velocity is v=F/D, where D is the appropriate drag coefficient. Integrating this equation of motion yields the solid lines for r(t) in FIG. 9B, and provides a very accurate description of the chain formation dynamics for a wide range of chain lengths and fluid viscosities.

The quantitative understanding of the dynamics of the nanowires' interactions demonstrated in this example has applications in the design of nanowires with specific behavior and response to both locally applied and external magnetic fields for use in any of the applications and devices described herein.

Example 6

Magnetic Separation of Cells

The efficacy of magnetic separation using magnetic nanowires was demonstrated as follows. NIH 3T3 cells cultured as described above were exposed to single-segment, unmagnetized Ni nanowires functionalized with rat-tail collagen, and incubated overnight. The wire concentration was chosen such that approximately 50% of the cells had one or more wires bound to them. The cells were than detached from the dishes by exposure to trypsin following standard techniques. Two-ml aliquots of the cells in suspension were placed in 10-ml plastic centrifuge cuvettes. The cuvettes were then brought in close proximity to a pair of small rear-earth permanent magnets for 5 minutes. The magnets were oriented with their poles anti-aligned to maximize the magnetic field gradient and hence the force on the nanowires, which become magnetized as well by exposure to this field. Visible clumps of wires and cells can be observed collecting near the pole faces of the magnets. The supernatant was then removed by pipetting and collected in a culture dish. This dish contained a large number of cells, of which less than 5% were bound to nanowires. Meanwhile, fresh medium was placed in the cuvette, and the magnets removed, which allowed the cells that had been immobilized to be collected. Of these, over 95% were found to be bound to one or more nanowires. This example demonstrates that cells bound to magnetic nanowires can be separated from cells that are not so bound.

Example 7

Magnetic Trapping of Multicomponent Nanowires

Figure 10:
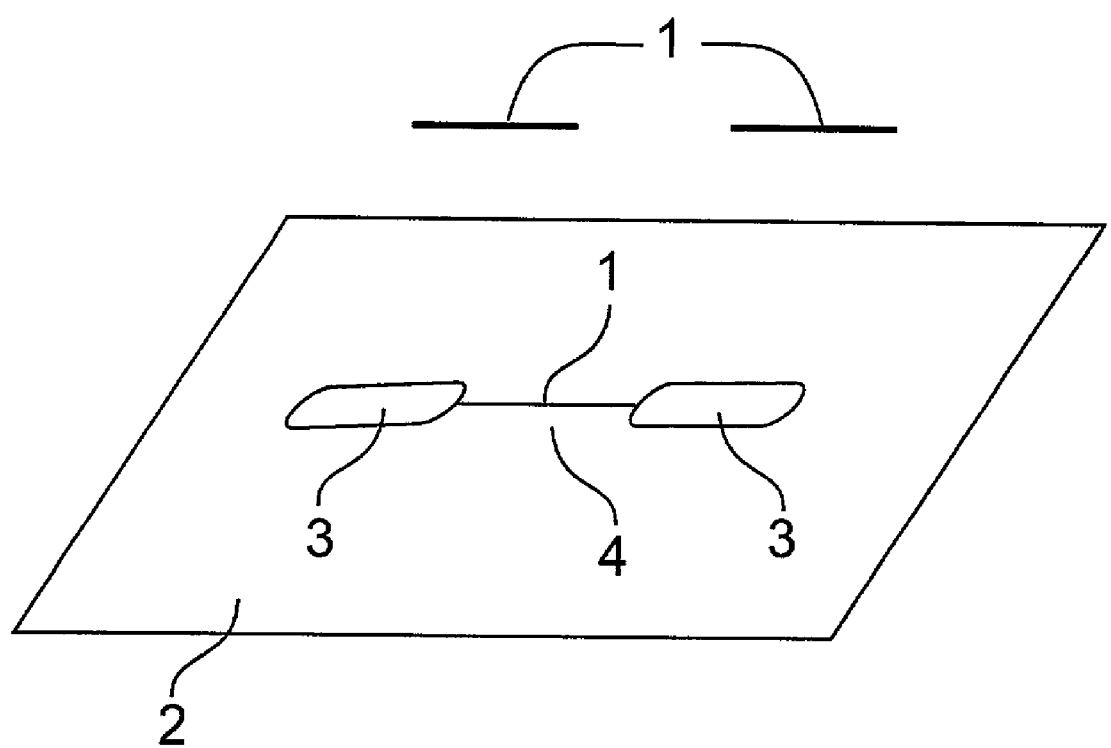
FIG. 10. Schematic representation of the magnetic trapping process. 1=magnetic nanowires; 2=substrate; 3=lithographically fabricated magnets; 4=gap between lithographically fabricated magnets.
Figure 11A:
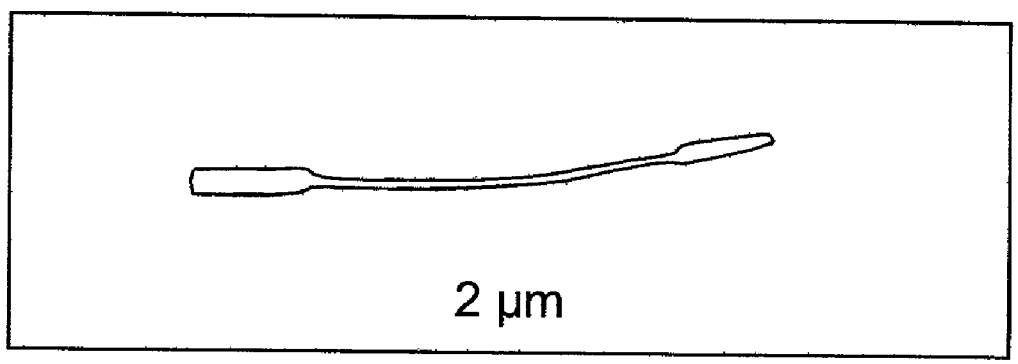
FIG. 11A-C. (a) Scanning electron microscope (SEM) image of a 3-segment Pt—Ni—Pt nanowire. The central Ni segment is 8 μm long, and the Pt segments are each 2 μm long. (b) A plan-view SEM image of a Pt—Ni—Pt nanowire trapped by elliptical Ni magnetic electrodes. The vertical bars are Au leads for electrical measurements. (b) Close-up SEM image of a trapped nanowire, with the substrate tilted 70°.
Figure 11B:
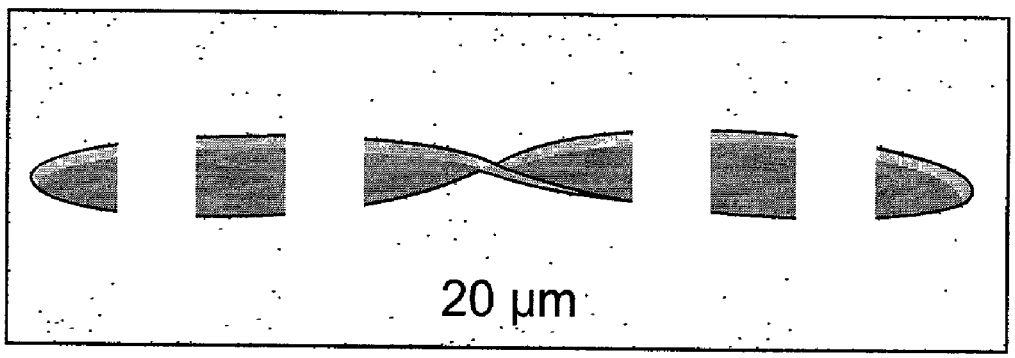
Figure 11C:
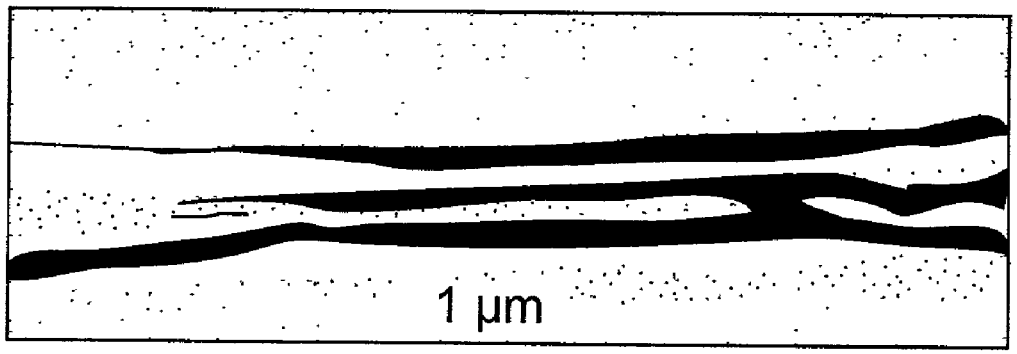

Magnetic trapping of Ni and Pt—Ni—Pt nanowires between planar magnetic micro-electrodes has been demonstrated. In this process, which is illustrated schematically in FIG. 10, magnetic nanowires 1 in a fluid suspension are allowed to settle onto a substrate 2 that contains lithographically patterned magnetic features 3. The local magnetic fields produced by these features influence the distribution of the nanowires on the substrate, and the nanowires can be made to bridge a gap 4 between closely spaced features, which behave as "magnetic electrodes." A single three-component nanowire is shown in FIG. 11A, and a trapped nanowire is shown in FIGS. 11B and 11C. The trapping process can be tuned by varying the concentration of nanowires in suspension and by applying an external magnetic field. The use of three-component nanowires with Pt end-segments yields low-resistance Ohmic electrical contacts between the nanowires and the magnetic electrodes.

This example demonstrates that magnetic nanowires can be directed to specific locations on a substrate or on the surface of an integrated circuit chip by localized magnetic fields produced by features, structures, or devices on that substrate or chip. Further, electric currents may be passes efficiently through these trapped nanowires for a variety of measurement or device engineering purposes.

Example 8

Magnetic Trapping of Cells Bound to Nanowires

The ability to use magnetic trapping of nanowires to bring cells to specific locations on a substrate was demonstrated as follows. Ni nanowires, 20 microns long and 300 nm in diameter, were functionalized with rat-tail collagen, and bound to NIH 3T3 cells, as described in Example 7. The cells were detached from the surface on which they had been cultured by exposure to trypsin, and suspended in fresh culture medium. These cells were magnetically separated as described in example 7. The cells containing magnetic nanowires were then allowed to settle onto a glass substrate with pairs of 8×80 micron magnetized Ni ovals. After settling, some of these cells are attracted into the gaps between ovals by the ovals' magnetic fields, where they become trapped by the magnetic forces between the ovals and the nanowires to which they are bound. This demonstrates the ability to manipulate the locations of individual cells using magnetic nanowires. This technique could be used to bring cells into contact with microelectronic circuits at specific locations in controlled ways.

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

REFERENCES

1. G. E. Possin, Rev. Sci. Instrum. 41, 772 (1970).
2. G. E. Possin, Physica 55, 339 (1971).
3. W. D. Williams and N. Giordano, Rev. Sci. Instrum. 55, 410 (1984).
4. J. T. Madsen and N. Giordano, Phys. Rev. B 31, 6395 (1985).
5. C. R. Martin, Science 266, 1961 (1994).
T. M. Whitney, J. S. Jiang, P. C. Searson, and C. L. Chien, Science 261, 1316 (1993).
7. L. Piraux, S.Dubois, E. Ferain, R. Legras, K. Ounadjela, J. M. George, J. L. Maurice, and A. Fert, J. Magn. Magn. Mater. 165, 352 (1997).
8. R. Ferre, K. Ounadjela, J. M. George, L. Piraux, and S. Dubois, Phys. Rev. B 56, 14066 (1997).
9. L. Sun, P. C. Searson, and C. L. Chien, Appl. Phys. Lett. (1999).

10. L. Piraux, J. M. George, J. F. Despres, C. Leroy, E. Ferain, R. Legras, K. Ounadjela, and A. Fert, Appl. Phys. Lett. 65, 2484 (1994).
11. A. Blondel, J. P. Meier, B. Boudin, and J.-Ph. Ansermet, Appl. Phys. Lett. 65, 3019, (1994).
12. K. Liu, K. Nagodawithana, P. C. Searson, and C. L. Chien, Phys. Rev. B 57, 7381 (1995).
13. P. B. Price and R. M. Walker, J. Appl. Phys. 33, 3400 (1962).
14. P. B. Price and R. M. Walker, J. Appl. Phys. 33, 3407 (1962).
15. C. P. Bean, M. V. Doyle, and G. Entine, J. Appl. Phys. 41, 1454 (1970).
16. R. L. Fleischer, P. B. Price and R. M. Walker, *Nuclear Tracks in Solids*, University of California, Berkeley (1975).
17. B. E. Fischer and R Spohr, Rev. Mod. Phys. 55, 907 (1983).
18. N. Tsuya, Y. Saito, H. Nakamura, S. Hayano, A. Furugohri, K. Ohta, Y. Wakui, and T. Tokushima, J. Mag. and Magnetic Materials 54, 1681 (1986).
19. M. Saito, M. Kirihara, T. Tanigushi, and M. Miyagi, Appl. Phys. Lett. 55, 607 (1989).
20. R. O'Barr, M. Lederman, and S. Schultze, J. Appl. Phys. 79, 6101 (1996).
21. P. P. Nguyen and R. J. Tonnuci, Mater. Res. Soc. Symp. Proc. 431, 421 (1996).
22. M. D. Stiles, "Interlayer Exchange Coupling", J. Magn. Mater. 200, 322 (1999)

We claim:

1. A magnetic nanowire comprising:
a plurality of segments, wherein said segments are formed from metal or metal alloys, and wherein at least one of said plurality of segments is magnetic; and
functional groups associated with at least one of said segments or ligands associated with at least one of said segments.

2. The magnetic nanowire of claim 1 wherein said segments are formed from a material selected from the group consisting of platinum, iron, cobalt, nickel, gold, silver, copper, iron oxide, copper oxide, zinc oxide, and alloys thereof.

3. The nanowire of claim 1 wherein said functional group is selected from the group consisting of thiols, disulfides, cyanides, amines, carboxylic acids, phosphonates, siloxanes, and hydroxamic acids.

4. The nanowire of claim 1 wherein said ligand is selected from the group consisting of proteins, fibronectin, DNA, RNA, enzymes, ribozymes, hydrophobic materials, hydrophilic materials, cells, tissue, microorganisms, bacteria, viruses, and chemoattractants.

5. The nanowire of claim 1 wherein at least one of said segments is formed from a fluorescent or photoluminescent material.

6. The nanowire of claim 1 wherein at least one of said segments has an associated photoluminescent label.

7. The nanowire of claim 1 wherein a different functional group or ligand is associated with each of two or more of said plurality of segments.

8. The magnetic nanowire of claim 1, wherein said functional groups or ligands are spatially resolved from each other along a length of said nanowire.

9. A method of forming a functionalized magnetic nanowire, comprising:
providing a magnetic nanowire having a plurality of segments, wherein said segments are formed from metal or metal alloys, and wherein at least one of said plurality of segments is magnetic,
associating functional groups or ligands with at least of one said segments, wherein said step of associating forms a functionalized magnetic nanowire.

10. The method according to claim 9 wherein said segments are formed from a material selected from the group consisting of platinum, iron, cobalt, nickel, gold, silver, copper, and iron oxide, $Cu_2O$, zinc oxide, and alloys thereof.

11. The method according to claim 9 wherein said functional group is selected from the group consisting of non-adhesive compounds, thiols, disulfides, cyanides, carboxylic acids, phosphonates, siloxanes, and hydroxamic acids.

12. The method according to claim 9 wherein said ligand is selected from the group consisting of proteins, DNA, RNA, enzymes, ribozymes, hydrophobic materials, hydrophillic materials, cells, tissue, microorganisms, bacteria, viruses, fibronectin, and chemoattractants.

13. The method according to claim 9 wherein at least one of said segments is formed from a fluorescent or photoluminescent material.

14. The method of claim 9 wherein at least one of said segments has an associated photoluminescent label.

15. A magnetized cell, comprising,
a cell, and
an associated magnetic nanowire, wherein said magnetic nanowire comprises a plurality of segments, wherein said segments are formed from metal or metal alloys, and wherein at least one of said plurality of segments is magnetic; and
functional groups associated with at least one of said segments or ligands associated with at least one of said segments.

16. A magnetic nanowire consisting of:
one or more segments, wherein said segments are formed from metal or metal alloys, and wherein at least one of said one or more segments is magnetic; and
functional groups associated with at least one of said segments or ligands associated with at least one of said segments.

17. A magnetic nanowire comprising:
a plurality of segments, wherein said segments are formed from metal or metal alloys, and wherein at least one of said plurality of segments is magnetic, and wherein a diameter of said magnetic nanowire is from 10 to 300 nanometers; and
functional groups associated with at least one of said segments or ligands associated with at least one of said segments.

* * * * *